United States Patent [19]

Young

[11] Patent Number: 4,554,925

[45] Date of Patent: Nov. 26, 1985

[54] NUCLEAR MAGNETIC RESONANCE IMAGING METHOD

[75] Inventor: Ian R. Young, Sunbury-on-Thames, England

[73] Assignee: Picker International, Ltd., Wembley, England

[21] Appl. No.: 508,480

[22] Filed: Jun. 27, 1983

[30] Foreign Application Priority Data

Jul. 7, 1982 [GB] United Kingdom ............. 8219628

[51] Int. Cl.$^4$ ............................................. A61B 5/05
[52] U.S. Cl. ......................................... 128/653; 324/309
[58] Field of Search ............ 128/653, 804, 654, 659; 324/315, 309

[56] References Cited

U.S. PATENT DOCUMENTS 3,525,928  8/1970  Nagao et al. ..................... 324/315
4,204,549  5/1980  Paglione .......................... 128/804

FOREIGN PATENT DOCUMENTS 47-32774  6/1972  Japan ............................. 324/315
2037996  7/1980  United Kingdom ............ 128/653

OTHER PUBLICATIONS

Moberly et al., *Application of Squid Magnetometer to Nuclear Magnetic Thermometry*, IEEE Transactions on Magnetics, vol. MAG-13, No. 1, Jan. 1977, pp. 358–360.

Hensel et al., *A Pulsed Nuclear Magnetic Resonance Thermometer for Use Below 100 mk*, Cryogenics, vol. 14, No. 3, Mar. 1974, pp. 121–131.

Primary Examiner—Kyle L. Howell
Assistant Examiner—Ruth S. Smith
Attorney, Agent, or Firm—Watts, Hoffmann, Fisher & Heinke Co.

[57] ABSTRACT

A nuclear magnetic resonance imaging apparatus associated with heat treatment means (45) and arranged to examine material subjected to heat treatment. The heat treatment means may be automatically controlled in dependence on any output produced by the imaging means, and/or manually controlled by an operator viewing a visual display (33) produced by the imaging means. The heat treatment means may be hyperthermia treatment means for treating diseased tissue of a patient.

5 Claims, 2 Drawing Figures

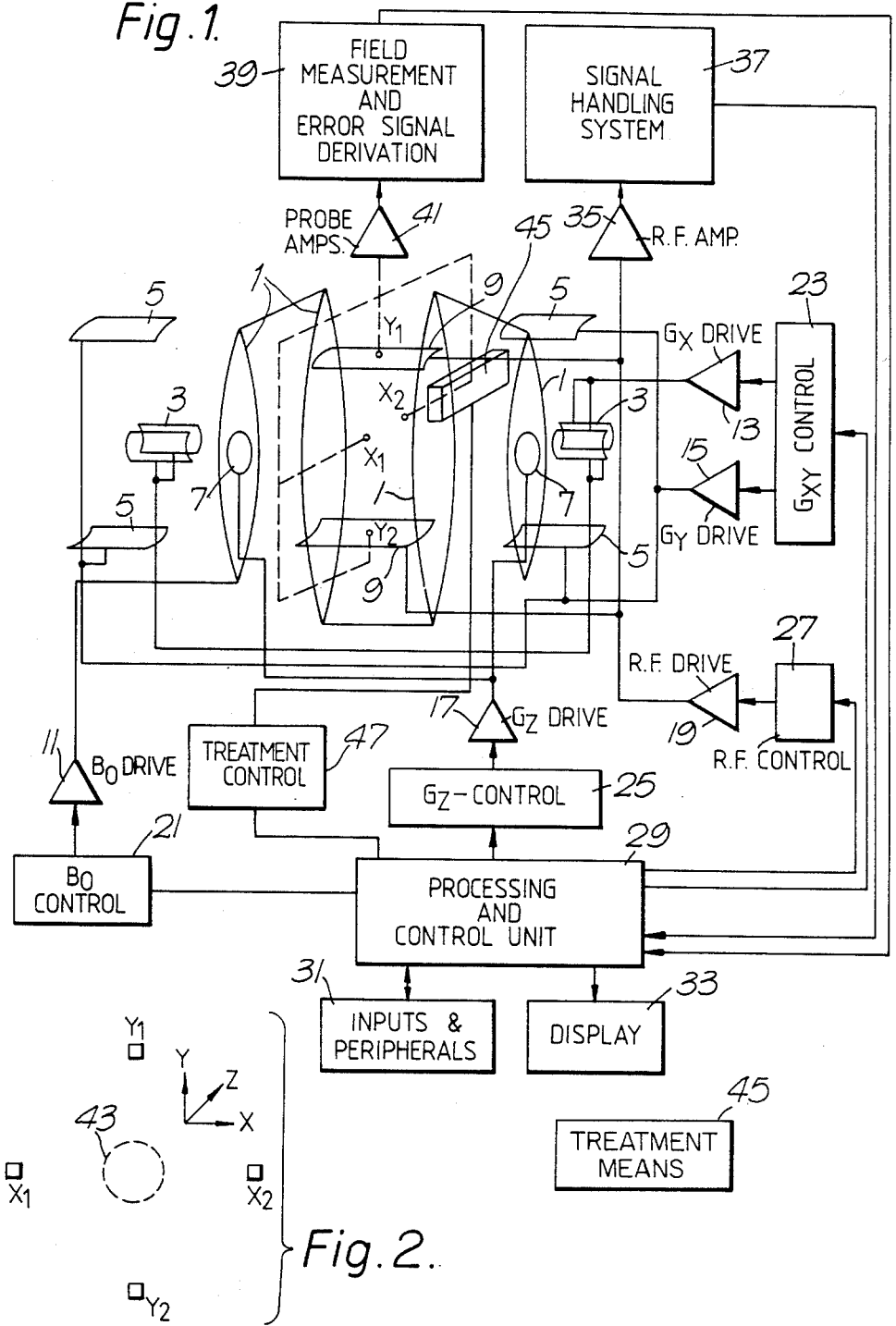

NUCLEAR MAGNETIC RESONANCE IMAGING METHOD

This invention relates to a nuclear magnetic resonance (NMR) imaging method.

NMR imaging can be used to examine the spatial distribution over a selected cross-sectional slice or volume of a body of a chosen quantity, for example, the density of chosen protons such as hydrogen nuclei, or NMR spin relaxation time constants. Such distributions are similar to, although of different significance from, the distributions of X-ray attenuation provided by computerized X-ray tomography systems.

According to the present invention an NMR imaging apparatus is associated with heat treatment means and is arranged to examine material subjected to treatment by said means.

The ability of an NMR imaging apparatus to examine material subjected to heat treatment arises from the fact that in a simple liquid the NMR spin lattice relaxation time constant ($T_1$) is a function of temperature, the relationship being of the form $$(1/T_1) \alpha (n/T)$$

where T is absolute temperature; and n is the viscosity of the liquid.

The viscosity of a simple liquid is highly dependent on temperature, so that, for example for water, a 12% change in $T_1$ may be expected for a temperature rise of 35° C. to 40° C.

Hence, an apparatus in accordance with the invention may be used to monitor accurately, on-line, whilst the heat treatment is being applied, the heating effect of the heat treatment on the material being treated.

The invention finds particular application where the heat treatment means is a hyperthermia treatment means.

Hyperthermia treatment comprises subjecting material, more especially diseased tissue of a patient, to microwave energy so as to raise the temperature of the material. In the case of diseased tissue, the treatment is typically such as to raise the temperature of the tissue by about 6° C., i.e. to about 43° C. for human tissue, sufficient to denature protein in the tissue.

It is most important in hyperthermia treatment that only the target diseased tissue, and not healthy tissue, should be heated. A method in accordance with the invention enables this to be successfully achieved.

One NMR imaging apparatus utilized in accordance with the invention will now be described, by way of example, with reference to the accompanying drawing in which:

FIGS. 1 and 2 illustrate the apparatus diagrammatically.

The apparatus is to a large extent of conventional form, for example, as described in United Kingdom patent specification No. 1,578,910 or No. 2,056,078 to which reference should be made for a fuller description of the apparatus.

The essential features of such apparatus and its method of operation, in so far as is necessary for an understanding of the present invention, are as follows:

The apparatus includes a first coil system whereby a magnetic field can be applied to a body to be examined in a given direction, normally designated the Z-direction, with a gradient in any one or more of the three orthogonal directions i.e. X, Y and Z directions.

Referring to FIG. 1, the first coil system comprises coils 1 which provide a steady uniform magnetic field $B_o$ in the Z-direction; coils 3 which provide a magnetic field gradient $G_x$ in the X-direction, coils 5 which provide a magnetic field gradient $G_y$ in the Y-direction; and coils 7 which provide a magnetic field gradient $G_z$ in the Z-direction.

In addition, the apparatus includes a second coil system 9 whereby RF magnetic fields can be applied to the body under examination in a plane normal to the direction of the magnetic field produced by the first coil system, and whereby RF magnetic fields resulting from nuclei in the body under examination which have been excited to nuclear magnetic resonance with a spin vector component other than in the Z-direction can be detected.

In the drawing a single pair of coils 9 is shown for both applying and detecting RF fields, but in certain circumstances it may be preferable to provide separate coils for detecting the RF fields.

The various coils 1, 3, 5, 7 and 9 are driven by $B_o$, $G_x$, $G_y$, $G_z$ and RF drive amplifiers 11, 12, 13, 15, 17 and 19 respectively, controlled by $B_o$, $G_{xy}$, $G_z$ and RF control circuits 21, 23, 25 and 27 respectively. These circuits may take various forms which are well known to those with experience of NMR equipment and other apparatus using coil induced magnetic fields.

The circuits 21, 23, 25 and 27 are controlled by a central processing and control unit 29 with which are associated inputs and other peripherals 31, for the provision of commands and instructions to the apparatus, and a display 33.

The NMR signals detected by the coils 9 are applied via an amplifier 35 to a signal handling system 37. The signal handling system is arranged to make any appropriate calibration and correction of the signals, but essentially transmits the signals to the processing and control unit 29 wherein the signals are processed for application to the display to produce an image representing the distribution of an NMR quantity in the body being examined.

It will be appreciated that whilst shown separately to clarify the present description, the signal handling system 37 may conveniently form part of the unit 29.

The apparatus also includes field measurement and error signal circuits 39 which receive signals via amplifiers 41 from field probes $X_1$, $X_2$, $Y_1$ and $Y_2$ which are disposed at suitable positions in relation to a slice 43 of the body being examined, as illustrated in FIG. 2, to monitor the applied magnetic fields.

In accordance with the present invention the apparatus further includes hyperthermia treatment means 45 whereby a selected region of the body under examination may be subjected to hyperthermia treatment. The treatment means 45 operates under control of a control means 47 which in turn may be controlled by the central processing control unit 29, as further described below.

The hyperthermia treatment means typically comprises means such as a waveguide injector, for direct injection of microwave energy into a selected region of the body under examination. Alternatively, the hyperthermia treatment means may comprise one of or more microwave energy radiators which are operated so as to minimise the heat produced in all except an internal target region of the body, for example, by mechanical movement in the case of a single radiator, or by appropriate switching in the case of a plurality of fixed radiators.

In use the apparatus is operated in well known manner to obtain an image representative of the spatial variation of the NMR spin lattice relaxation time ($T_1$) of appropriate protons, normally hydrogen nuclei, in a region of the body including the region which is to be subjected to hyperthermia treatment.

Such an image may for example be obtained using a so-called inversion recovery sequence and any desired image reconstruction technique such as a back projection technique or a Fourier transformation technique.

When an image has been established the hyperthermia treatment means is switched on and the NMR image is used to monitor the spin lattice relaxation time and hence the temperature of the material being subjected to the hyperthermia treatment. The hyperthermia treatment means may then be controlled so as to prevent excessive heating of any part of the imaged area of the body e.g. so that areas not being treated do not approach 43° C. and so that the areas to be treated are not excessively heated. To this end the control means 47 may be controlled automatically by an output signal produced by the processing and control unit. Alternatively or additionally, a visual representation of spin lattice relaxation time image may be displayed on the display 33 and appropriate action taken to prevent excessive heating by an operator viewing the image. The image may also be used by the operator to position the hyperthermia treatment means so that the desired target area of the body is subjected to hyperthermia treatment.

The processing and control unit 33 may also be arranged to control the imaging and hyperthermia treatment functions of the apparatus so as to minimize interference of the hyperthermia function with the imaging function.

It will be appreciated that whilst in the embodiment of the invention described above by way of example the heat treatment involves raising the temperature of a region of a body, the invention is equally applicable to apparatus in which the heat treatment means cools a region of a body. The term heat treatment as used in the present specification and claims should therefore be interpreted accordingly.

It is further pointed out that whilst in general the particular NMR parameter which it is desirable to examine in an apparatus according to the invention is spin lattice relaxation time, it may in certain circumstances be desirable to examine, additionally or alternatively, other NMR parameters. Such alternative parameters may be examined not only to obtain a better representation of temperature variation, but also to obtain a better representation of the body structure, thereby to facilitate the identification of different regions of the body being examined.

I claim:

1. A method for treating animal tissue, in vivo, said method comprising the steps of:
    (a) changing the temperature of tissue in an internal region of an animal body relative to temperature of tissue in an adjacent region;
    (b) operating a nuclear magnetic resonance imaging apparatus substantially simultaneously with performance of said temperature changing step to produce a continuous spatial mapping representation of temperature within said body over a portion of said body at least partially including a part of said internal region upon which said temperature changing step is performed;
    (c) controlling said temperature changing step as a function of temperature indication produced in said nuclear magnetic resonance operating step.

2. The method of claim 1, wherein said temperature changing step comprises:
    elevating the temperature of said internal region of said body to approximately 43° Centigrade.

3. The method of claim 2, further comprising the further step of:
    simultaneously maintaining the temperature of a region adjacent said internal region at a temperature substantially less than 43° Centigrade.

4. The method of claim 3, wherein said step of controlling said temperature changing step is performed manually.

5. A method of in vivo treatment of a living human body, said method comprising the steps of:
    (a) positioning a hyperthermia treatment apparatus relative to the human body for raising the temperature of a predetermined internal region of the body relative to the temperature of an adjacent region when said hyperthermia apparatus is operated;
    (b) positioning a nuclear magnetic resonance imaging apparatus relative to the human body and producing, an image depicting a continuous spatial mapping representation of temperature within a portion of the body at least partially including said predetermined internal region, and
    (c) simultaneously operating both said hyperthermia treatment apparatus and said nuclear magnetic resonance imaging apparatus as specified in steps (a) and (b);
    (d) controlling the operation of said hyperthermia treatment apparatus as a function of a temperature indication produced by operation of said nuclear magnetic resonance imaging system.

* * * * *